United States Patent [19]

MacLeod

[11] Patent Number: 5,342,761
[45] Date of Patent: Aug. 30, 1994

[54] ONCOFETAL GENE, GENE PRODUCT AND USES THEREFOR

[75] Inventor: Carol L. MacLeod, San Diego, Calif.

[73] Assignee: Research Development Foundation, Carson City, Nev.

[21] Appl. No.: 590,894

[22] Filed: Oct. 1, 1990

[51] Int. Cl.$^5$ .................. C12N 15/00; A61K 39/00; C12P 21/06; C07K 15/00
[52] U.S. Cl. .................. 435/69.1; 435/69.3; 435/320.1; 435/172.3; 435/252.33; 530/350; 536/23.1; 536/24.31
[58] Field of Search .................. 435/69.1, 69.3, 320.1, 435/172.3; 530/350; 536/23.1; 424/88

[56] References Cited

PUBLICATIONS

Hedrick et al Nature 308: 149–153 (1984).
Hays et al, Int. J. of Cancer 38, 597–601 (1986).
McMichael et al Leukocyte typing III, pub. Oxford Univ. Press (1987) pp. 31–62 vol. 5.1.
Wilkinson et al, Dev. Biol. 141: 451–455 (1990).

*Primary Examiner*—David L. Lacey
*Assistant Examiner*—T. M. Nisbet
*Attorney, Agent, or Firm*—Benjamin Adler

[57] ABSTRACT

The present invention provides a novel cDNA sequence (Pem), a gene product protein (Seq. id No. 1), and uses for this novel cDNA Sequence and the Pem gene product. The DNA sequence and recombinant DNA molecules of this invention are characterized in that each codes for a novel protein having the following characteristics: (1) is expressed by T lymphoma cells, (2) is not expressed in normal thymus, activated spleen cells, gut associated lymphoid tissue, or bone marrow, and is not detectable in adult brain, liver, large intestine or ovary, (3) is expressed in immortalized or cancerous cell lines, and (4) is expressed in embryonic development.

9 Claims, 3 Drawing Sheets

```
                    20.2 (PEM) cDNA and PREDICTED PROTEIN SEQUENCE

GAA GAG CCA AAC AGC CAT CTC CCT GCA CAG TCC TTC AAG CTC   42
  1    Glu Glu Pro Asn Ser His Leu Pro Ala Gln Ser Phe Lys Leu

ACC TCC TGC CTT CCG TGG ACA AGA GGA AGC ACA AAG AAT CAT   84
  15   Thr Ser Cys Leu Pro Trp Thr Arg Gly Ser Thr Lys Asn His
                 (C)                              (C)
       CCA GGT ATG GAA GCT GAG GGT TCC AGC CGC AAG GTC ACC AGG   126
  29   Pro Gly MET Glu Ala Glu Gly Ser Ser Arg Lys Val Thr Arg
                              (C C)              (AG)
       CTA CTC CGC CTG GGA GTC AAG GAA GAC TCG GAA GAA CAG CAT   168
  43   Leu Leu Arg Leu Gly Val Lys Glu Asp Ser Glu Glu Gln His

GAT GTG AAA GCA GAG GCT TTC TTC CAG GCT GGA GAG GGG AGA   210
  57   Asp Val Lys Ala Glu Ala Phe Phe Gln Ala Gly Glu Gly Arg

GAT GAG CAA GGT GCA CAG GGC CAG CCT GGA GTG GGA GCG GTG   252
  71   Asp Glu Gln Gly Ala Gln Gly Gln Pro Gly Val Gly Ala Val

GGA ACA GAA GGC GAA GGA GAA GAA TTA AAT GGA GGA AAA GGC   294
  85   Gly Thr Glu Gly Glu Gly Glu Glu Leu Asn Gly Gly Lys Gly
             (CK)
       CAC TTT GGT CCT GGT GCT CCT GGT CCT ATG GGT GAT GGG GAC   336
  99   His Phe Gly Pro Gly Ala Pro Gly Pro Met Gly Asp Gly Asp

AAG GAT AGT GGC ACC AGG GCT GGT GGT GTG GAG CAG GAA CAA   378
 113   Lys Asp Ser Gly Thr Arg Ala Gly Gly Val Glu Gln Glu Gln

AAT GAG CCA GTT GCT GAG GGC ACT GAG AGC CAG GAG AAT GGA   420
 127   Asn Glu Pro Val Ala Glu Gly Thr Glu Ser Gln Glu Asn Gly

AAT CCT GGG GGT AGG CAG ATG CCC CTC CAG GGC TCT AGG TTC   462
 141   Asn Pro Gly Gly Arg Gln Met Pro Ser Arg Ala Leu Gly Ser

GCC CAG CAT CGA CTG AGG GAA CTG GAG TCC ATT TTG CAG CGC   504
 155   Pro Ser Tyr Arg Leu Arg Glu Leu Glu Ser Ile Leu Gln Arg
             (C)
       ACT AAT TCC TTT GAT GTC CCA AGG GAG GAT CTT GAT AGA CTG   546
 169   Thr Asn Ser Phe Asp Val Pro Arg Glu Asp Leu Asp Arg Leu

ATG GAT GCC TGT GTG TCC AGA GTG CAG AAT TGG TTT AAG ATC   588
 183   Met Asp Ala Cys Val Ser Arg Val Gln Asn Trp Phe Lys Ile
                                                        (C)
       AGG AGG GCT GCG GCC AGA AGA AAC AGG AGG AGG GCA ACA CCA   630
 197   Arg Arg Ala Ala Ala Arg Arg Thr Arg Arg Arg Ala Thr Pro
                         (C)                 (AG)
       GTC CCT GAA CAT TTT AGA GGA ACA TTC GAG TGT CCT GCT TGT   672
 211   Val Pro Glu His Phe Arg Gly Thr Phe Glu Cys Pro Ala Cys

CGT GGA GTG AGA TGG GGA GAA AGA TGC CCT TTT GCG ACA CCG   714
 225   Arg Gly Val Arg Trp Gly Glu Arg Cys Pro Phe Ala Thr Pro
                                                        (C)
       AGA TTT TGA TTT GAT CAC ATA TGC CGG CTA TGA CAG CCC TTA   756
 239   Arg Phe

CTT TTC AAG AAT TCA GCA ATA AAG AGG TGG ATT CCC AGT ATG   798
       TTT GTT CCA TTA CCT CTA TGA TTA TTA AAA TAT TGA TAC A(x)   838

C = Predicted glycosylation site
  AG & CK = Predicted phosphorylation site
  AATAAA = Predicted polyadenylation site Number on left refers to amino acid sequence, on right to DNA sequence
```

20.2 (PEM) cDNA and PREDICTED PROTEIN SEQUENCE

```
     GAA GAG CCA AAC AGC CAT CTC CCT GCA CAG TCC TTC AAG CTC    42
 1   Glu Glu Pro Asn Ser His Leu Pro Ala Gln Ser Phe Lys Leu

ACC TCC TGC CTT CCG TGG ACA AGA GGA AGC ACA AAG AAT CAT    84
15   Thr Ser Cys Leu Pro Trp Thr Arg Gly Ser Thr Lys Asn His
          |                              |
         (C)                            (C)
     CCA GGT ATG GAA GCT GAG GGT TCC AGC CGC AAG GTC ACC AGG   126
29   Pro Gly MET Glu Ala Glu Gly Ser Ser Arg Lys Val Thr Arg
                                  |   |              |
                                 (C   C)           (AG)
     CTA CTC CGC CTG GGA GTC AAG GAA GAC TCG GAA GAA CAG CAT   168
43   Leu Leu Arg Leu Gly Val Lys Glu Asp Ser Glu Glu Gln His

GAT GTG AAA GCA GAG GCT TTC TTC CAG GCT GGA GAG GGG AGA   210
57   Asp Val Lys Ala Glu Ala Phe Phe Gln Ala Gly Glu Gly Arg

GAT GAG CAA GGT GCA CAG GGC CAG CCT GGA GTG GGA GCG GTG   252
71   Asp Glu Gln Gly Ala Gln Gly Gln Pro Gly Val Gly Ala Val

GGA ACA GAA GGC GAA GGA GAA GAA TTA AAT GGA GGA AAA GGC   294
85   Gly Thr Glu Gly Glu Gly Glu Glu Leu Asn Gly Gly Lys Gly
             |
           (CK)
     CAC TTT GGT CCT GGT GCT CCT GGT CCT ATG GGT GAT GGG GAC   336
99   His Phe Gly Pro Gly Ala Pro Gly Pro Met Gly Asp Gly Asp

AAG GAT AGT GGC ACC AGG GCT GGT GGT GTG GAG CAG GAA CAA   378
113  Lys Asp Ser Gly Thr Arg Ala Gly Gly Val Glu Gln Glu Gln

AAT GAG CCA GTT GCT GAG GGC ACT GAG AGC CAG GAG AAT GGA   420
127  Asn Glu Pro Val Ala Glu Gly Thr Glu Ser Gln Glu Asn Gly

AAT CCT GGG GGT AGG CAG ATG CCC CTC CAG GGC TCT AGG TTC   462
141  Asn Pro Gly Gly Arg Gln Met Pro Ser Arg Ala Leu Gly Ser
```

FIG. 1A

```
     GCC CAG CAT CGA CTG AGG GAA CTG GAG TCC ATT TTG CAG CGC   504
155  Pro Ser Tyr Arg Leu Arg Glu Leu Glu Ser Ile Leu Gln Arg
         |
        (C)
     ACT AAT TCC TTT GAT GTC CCA AGG GAG GAT CTT GAT AGA CTG   546
169  Thr Asn Ser Phe Asp Val Pro Arg Glu Asp Leu Asp Arg Leu

ATG GAT GCC TGT GTG TCC AGA GTG CAG AAT TGG TTT AAG ATC   588
183  Met Asp Ala Cys Val Ser Arg Val Gln Asn Trp Phe Lys Ile
                                                     |
                                                    (C)
     AGG AGG GCT GCG GCC AGA AGA AAC AGG AGG AGG GCA ACA CCA   630
197  Arg Arg Ala Ala Ala Arg Arg Thr Arg Arg Arg Ala Thr Pro
                                 |                   |
                                (C)                 (AG)
     GTC CCT GAA CAT TTT AGA GGA ACA TTC GAG TGT CCT GCT TGT   672
211  Val Pro Glu His Phe Arg Gly Thr Phe Glu Cys Pro Ala Cys

CGT GGA GTG AGA TGG GGA GAA AGA TGC CCT TTT GCG ACA CCG   714
225  Arg Gly Val Arg Trp Gly Glu Arg Cys Pro Phe Ala Thr Pro
                                                         |
                                                        (C)
     AGA TTT TGA TTT GAT CAC ATA TGC CGG CTA TGA CAG CCC TTA   756
239  Arg Phe

CTT TTC AAG AAT TCA GCA ATA AAG AGG TGG ATT CCC AGT ATG   798
     TTT GTT CCA TTA CCT CTA TGA TTA TTA AAA TAT TGA TAC A(x)  838
```

C = Predicted glycoslyation site
AG & CK = Predicted phosphorlyation site
AATAAA = Predicted polyadenylation site Number on left refers to amino acid sequence, on right to DNA sequence

FIG. 1B

ONCOFETAL GENE, GENE PRODUCT AND USES THEREFOR

FIELD OF THE INVENTION

This invention concerns a novel cDNA clone obtained from a T-lymphoma library. This novel cDNA clone, known as Pem, hybridizes to transcripts expressed in placenta and embryos in a stage-specific manner. The Pem cDNA sequence predicts an intracellular hydrophilic protein with no significant sequence similarity with other DNA or protein sequences. The DNA sequence and recombinant DNA molecules of this invention are characterized in that each codes for a novel protein having the following characteristics: (1) is expressed by T lymphoma cells, (2) is not expressed in normal thymus, activated spleen cells, gut associated lymphoid tissue, or bone marrow, and is not detectable in adult brain, liver, large intestine or ovary, (3) is expressed in immortalized or cancerous cell lines, and (4) is expressed in embryonic development. As may be appreciated from the disclosure to follow, the DNA sequence, recombinant DNA molecules and process for producing the novel protein expressed in embryonic development and the novel Pem protein in substantially pure form may be useful in manipulating the regulation of embryonic development, altering the tumorigenic phenotype and may also be useful for localizing metastatic foci of tumors containing the Pem oncogene.

BACKGROUND ART

Numerous genes have been identified in invertebrate organisms such as Drosophila melanogaster, Caenorhabditis elegans and Sacharomyces cerevisiae which participate in developmental events. In mammalian systems, only a few genes which play an integral role during development have been identified (Blau, (1988) Cell 53:673). For example, the muscle-specific genes, MyoD1 and myogenin, have served as important models of genetic control of murine differentiation. Somites and limb buds first express myogenin and MyoD1 on days 8 and 10 of gestation, respectively (Sasson, et al. (1989) Nature 341: 303-308) and are known to control the switch to the myoblast lineage in vitro (Davis, et al. (1987) Cell 51: 987-1000). The Hox-5 gene complex exhibits an interesting pattern of expression in murine limb buds after the 9th day of gestation (Dolle, et al. (1989) Nature 342: 161-111), although the function(s) of the encoded genes have yet to be defined. Few other genetic markers are known which tag cells in early and intermediate stages of murine development. For example, no gene has been associated uniquely with the initial process of segmentation, which occurs on day 8 of gestation in the mouse (for review, see Rossant and Joyner, (1989) Trends in Genetics 5: 277-283).

Immortalized and fully transformed cells frequently transcribe genes which are expressed in (and presumably influence) normal mammalian development (reviewed, Ruddon, (1987) Gene Derepression in Cancer Cells, in Cancer Biology, Oxford University Press, New York, pp 431-436). In some cases, these "oncofetal" genes do not appear to contribute to the neoplastic phenotype. For example, a-fetoprotein is expressed by trophoblast cells and by many tumor cells. In other cases, developmentally regulated genes play a primary role in the conversion of cells to the transformed phenotype. For example, the proto-oncogenes c-myc, c-src, c-fos, and c-fms are expressed during embryonic development, and have been shown to regulate developmental steps in vitro (for review, see Adamson, (1987) Placenta 8: 449-466).

In the development of the immune system, T lymphocytes are derived from precursor stem cells which enter the thymus to undergo differentiation and maturation. Many genes are either activated or repressed as the T cell passes through different stages of development within the thymus. For example, the cells acquire the IL-2 receptor, CD4, and/or CD8 on their surface during this time. These differentiation markers are important for T cell development and/or function. Many gene products are increased in their levels of expression in developing T lymphocytes. These include the T cell receptor for antigen as well as the markers CD4 and CD8. Many other antigens have served as T cell markers before their exact function in lymphocytes were known. Only recently has it been discovered that the T cell antigen Pgpl aids thymocytes in their homing to the thymus whereas T200 (CD45) serves as a component for intracellular signalling. Another T cell marker, Thyl, still has no known function associated with it.

The SL 12.4 cells exhibit a CD4/CD8 double negative phenotype and therefore resemble thymocytes at a relatively early stage of development. Furthermore, they do not express the T cell receptor alpha subunit. SL 12.4 cells, however, can be induced to stably express CD4 and CD8 on their surface after co-cultivation upon thymic epithelial monolayers. TCR-alpha mRNA is also induced after these treatments. Thus, it appears that SL 12.4 cells have the capacity to undergo differentiation and maturation. This unique in vitro biological system mimics, to some extent, the thymic microenvironment.

A number of genes have been identified which are first expressed in developing thymocytes. Many of these genes encode proteins which must be expressed for T cell precursors to become functional in the immune system, for example: 1) the TCR for antigen which is required for antigen recognition; 2) CD25 (the IL2 receptor) which must be expressed for the cells to respond to the cytokine IL2; 3) gene products important for signal transduction during antigen recognition, such as CD3, CD4, CDS, CD45, 4) some of the gene products involved in thymocyte homing to target organs, and 5) gene products involved in T cell activation (Fowlkes and Pardoll, Advances in Immunology 44:207-264 (1989); Hood et al., (1985) Cell 40, 225-229; Rothenberg and Lugo, Develop. Biol. 112, 1-17 (1985); Adkins et al., Ann. Rev. Immunol. 5:325-365 (1987); Crabtree, Science 243:343-355 (1989); Kwon and Weissman, Proc. Natl. Acad. Sci. USA 86:1963-1967 (1989). There is remarkable heterogeneity in thymocyte subsets which express different combinations of expressed genes. Gene expression has been analyzed in detail in many, but not all, of the numerous classes of thymocytes and it is likely that genes remain to be identified that encode products which function in T cell development and homing; particularly those which are expressed in numerically infrequent, transient progenitor thymocytes.

Due to the extensive heterogeneity of thymocytes, it is not feasible to obtain fractionated progenitor thymocytes in sufficient numbers or purity to fully characterize the cascade of gene expression which occurs during development. For this reason, lymphoma and leukemia cell lines have been used extensively to study gene expression in lymphoid development (Greaves, (1986) *Science* 234:697–704; Hanley-Hyde and Lynch (1986) *Ann. Rev. Immunol.* 4:621–649. A considerable body of literature indicates that numerically infrequent, transient progenitor cells are the target of transformation to malignancy; and further that some of the characteristics of the transformed target cells are preserved in the tumor cells. Unexpected gene expression in tumor cells was frequently dismissed as an aberration of transformation. However, careful analysis of "aberrant" gene expression in hematopoeitic tumor cells, has revealed rare subsets of normal progenitor cells which express such genes (Greaves, (1986) *Science* 234:697–704; Hanley-Hyde and Lynch (1986) *Ann. Rev. Immunol.* 4:621–649; Pierce and Speers (1988) *Cancer Res.* 48:1996–2004).

The heterogeneity of murine and human lymphoma cell lines derived from a single individual can result from differences in the extent of maturation reached by individual cells. The heterogeneity of established T lymphoma cell lines has been utilized to obtain closely related cell clones which differ in a limited number of characteristics. Hedrick, et al (Hedrick, et al., (1984) *Nature* 308:149–153), using subtraction cloning techniques, provided estimates that T and B, cells differ in the expression of about 100 genes. It is likely that closely related T lymphoma cells might differ in the expression of even fewer genes. Such cell clones provide an opportunity to work with pure populations of cells with defined and stable phenotypes which differ in a limited number of characteristics. The SL12 T lymphoma model system was developed and utilized in the present application to provide such a closely related cell population. (Hays et al., (1986) *Int. J. Cancer* 30:597–601; MacLeod, et al., (1984) *Cancer Research* 44:1784–1790; MacLeod, et al., (1985) *J. Nat. Cancer Inst* 74:875–882; MacLeod, et al., (1986) *Proc. Natl. Acad. Sci. USA* 83:6989–6993; Siegal, et al., (1987) *J. Exp. Med.* 166:1702–1715).

SL12.4 cells are similar to thymocytes at an intermediate stage of maturation (Fowlkes and Pardoll, (1989) *Advances in Immunol.* 44: 207–264). The two cell clones differ in their biological properties. SL12.4 cells generate extranodal tumors and are sensitive to glucocorticoid-induced lysis, whilst SL12.3 cells cause diffuse disseminated tumors resistant to lysis by glucocorticoids.

BRIEF DESCRIPTION OF THE INVENTION

The present invention provides a novel cDNA sequence, a gene product (Pem) protein, and uses for this novel cDNA sequence and the Pem gene product. In this invention, the sequence and expression characteristics of a novel gene represented by a cDNA clone (Pem) obtained from a T-lymphoma is described. Immortalized and transformed cell lines derived from several lineages express Pem transcripts. The DNA sequence and recombinant DNA molecules of this invention are characterized in that each codes for a novel protein having the following characteristics: (1) is expressed by T lymphoma cells, (2) is not expressed in normal thymus, activated spleen cells, gut associated lymphoid tissue, or bone marrow, and is not detectable in adult brain, liver, large intestine or ovary, (3) is expressed in immortalized or cancerous cell lines, and (4) is expressed in embryonic development. As may be appreciated from the disclosure to follow, the DNA sequence, recombinant DNA molecules and process for producing the novel protein expressed in embryonic development and the novel Pem protein in substantially pure form may be useful in manipulating the regulation of embryonic development, altering the tumorigenic phenotype and may also be useful for localizing metastatic foci of tumors containing the Pem oncogene.

Although the Pem gene is not detectably expressed in adult tissue, it is sequentially expressed during murine fetal development, first in early embryos and subsequently in extraembryonic tissues. The expression of Pem during fetal development and its presence in immortalized and neoplastic cell lines is consistent with the properties expected of an "oncofetal" gene. This Pem cDNA sequence may be useful as a marker of neoplastic cells and of cells participating in early embryonic development.

Further objects, features and advantages of the present invention will become apparent from a review of the detailed description of the preferred embodiments which follows, in view of the drawings, a brief description of which follows.

BRIEF DESCRIPTION OF THE DRAWINGS

FIG. 1(*a* and *b*) shows the DNA and predicted protein sequence of Pem cDNA.

DETAILED DESCRIPTION OF THE INVENTION

Figure 2:
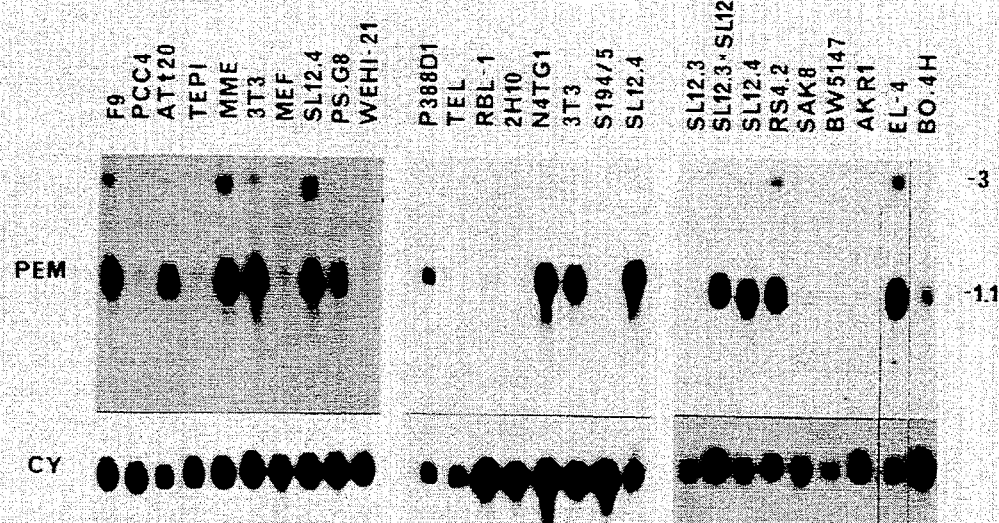
FIG. 2 demonstrates the Pem mRNA expression in cell lines.

In order that the invention herein described may be more fully understood, the following detailed description is set forth.

In the description the following terms are employed:

The term "host" as used herein is meant to include not only prokaryotes but also eukaryotes such as yeast and filamentous as well as plant and animal cells.

The term "prokaryote" is meant to include all bacteria which can be transformed with the DNA for the expression of the Pem or recombinant Pem proteins (rPemP) of the present invention.

The term "eukaryote" is meant to include all yeasts, fungi, animal and plant cells which can be transformed with the DNA for the expression of the Pem or recombinant Pem proteins of the present invention.

The DNA for the Pem proteins of the present invention can be derived from any mammalian species. All that is required is that the genetic sequence for the Pem protein (PemP) be expressed in the prokaryotic or eukaryotic organism. Preferred is the Pem DNA which expresses Pem protein(s) from mice. Especially preferred is the sequence of the Pem DNA which is immunologically cross reactive among multiple animal species (e.g., mice, rabbit, sea lion or human).

A recombinant DNA molecule coding for the Pem protein of the present invention can be used to transform a host using any of the techniques commonly known to those of ordinary skill in the art. Especially preferred is the use of a vector containing coding sequence for the Pem protein of the present invention for purposes of prokaryote transformation.

The T cell recombinant protein (rPem) of the invention could have more or less amino acids at its flanking ends as compared to the amino acid sequence of native Pem protein.

The term "substantially pure" when applied to the Pem protein of the present invention means that the polypeptide is essentially free of other proteins normally associated with the Pem protein in its natural state and exhibiting constant and reproducible electrophoretic or chromatographic response, elution profiles, and antigen activity. The term "substantially pure" is not meant to exclude artificial or synthetic mixtures of the Pem protein with other compounds.

Methods for preparing fused, operably linked genes and expressing them in bacteria are known and are shown, for example, in U.S. Pat. No. 4,366,246, herein incorporated by reference. The genetic constructs and methods described therein can be utilized for expression of Pem protein in prokaryotic or eukaryotic hosts.

Prokaryotic hosts may include Gram negative as well as Gram positive bacteria, such as *E. coli, S. tymphimurium, Serratia marcescens,* and *Bacillus subtillis.*

Eukaryotic hosts may include yeasts such as *Pichia pastoris* or mammalian cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Examples of promoters which can be used in the invention include, but are not limited to: rec A, trp, lac, tac, bacteriophage lambda pR or pL, MMTV, SV40. Examples of some of the plasmids or bacteriophage which can be used in the invention are listed in Maniatis et al., *Molecular Cloning,* Cold Spring Harbor Laboratories, 1982, and others are known to those of skill in the art and can be easily ascertained.

The invention extends to any host modified according to the methods described, or modified by any other methods, commonly known to those of ordinary skill in the art, such as, for example, by transfer of genetic material using a lysogenic phage, and which yield a prokaryote or eukaryote expressing the gene for the Pem protein.

A gene is a DNA sequence which encodes through its template or messenger RNA a sequence of amino acids characteristic of a specific peptide. The term cDNA includes genes from which the intervening sequences have been removed. By the term rDNA is meant a molecule that has been recombined by splicing cDNA or genomic DNA sequences in vitro.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance, neomycin resistance or ampicillin resistance. The word "vector" is sometimes used for cloning vehicle.

An expression vehicle is a vehicle similar to a cloning vehicle but which is capable of expressing a given structural gene in a host, normally under control of certain control sequences.

Hosts transformed with the Pem genome for the Pem protein are particularly useful for the production of Pem polypeptide and protein.

The Pem protein may comprise the entire amino acid sequence of the Pem protein or may comprise only a specific determinant. An animal immunized with Pem recombinant protein will produce antibodies which will bind to epitopes present on the recombinant or naturally occurring polypeptides. Thus, the commercial production of Pem-containing recombinant proteins can be carried out.

The term "individual" is meant to include any animal, preferably a mammal, and most preferably a rodent, cat, dog, cow or human.

Detectable labels may be any molecule which may be detected. Commonly used detectable labels are radioactive labels including, but not limited to, $^{32}P$, $^{14}C$, $^{125}I$, $^{3}H$ and $^{35}S$. Biotin labeled nucleotides can be incorporated into DNA or RNA by nick translation, enzymatic, or chemical means. The biotinylated probes are detected after hybridization using avidin/streptavidin, fluorescent, enzymatic or collodial gold conjugates. Nucleic acids may also be labeled with other fluorescent compounds, with immunodetectable fluorescent derivatives or with biotin analogues. Nucleic acids may also be labeled by means of attaching a protein. Nucleic acids cross-linked to radioactive or fluorescent histone Hl, enzymes (alkaline phosphatase and peroxidases), or single-stranded binding (ssB) protein may also be used.

Two cell clones derived from the SL12 T lymphoma cell line were chosen for the isolation of novel differentially expressed genes based on known differences in gene expression and on their different capacity to cause tumors in syngeneic host animals (Hays, et al., (1986) *Int. J.Cancer* 38:597–601; MacLeod, et al., (1984) *Cancer Research* 44:1784–1790; MacLeod, et al., (1985) *J. Nat. Cancer Inst.* 74:875–882; MacLeod, et al., (1986) *Proc. Natl. Acad. Sci. USA* 83:6989–6993; Siegal, et al., (1987) *J. Exp. Med.* 166:1702–1715; Weinroth, et al., (1985) *Cancer Research* 45:4804–4809; Wilkinson, et al., (1988) *EMBO J.* 7:101–109 and Table 1 for a summary of phenotypes). The SL12.3 cell line expresses very few of the genes required for T cell function, it is highly malignant in syngeneic animals and forms diffuse, aggressive tumors. In contrast, SL12.4 cells express mRNAs for all the components of the TCR/CD3 complex except TCR-alpha, and in several respects, the cells are similar to thymocytes at an intermediate stage in thymocyte development. SL12.4 cells are much less tumorigenic and induce prominant extranodal tumors.

To isolate cDNA clones representing genes expressed exclusively in SL12.4 cells and not in SL12.3 cells, a combination of subtraction hybridization-enriched probes and classical differential screening was used (similar to Filmus, et al., (1989) *Mol. Cell. Biol.* 8: 4243–4249, as described in detail elsewhere (MacLeod et al., (1990) *Cell Growth Differ.* 1: 271–279).

By providing the DNA sequences, and recombinant DNA molecules, the present invention also provides probes and methods to identify cells containing or lacking these sequences, and means to administer these sequences to cells lacking these sequences.

Additionally, the present invention provides a means to inhibit the expression of the novel Pem sequence by providing to a cell containing the normal Pem DNA sequence, an antisense RNA sequence or the DNA encoding said antisense KNA which can bind to and therefore block the synthesis of the RNA encoding the novel protein of the present invention. It will also be apparent to one of skill in the art from this disclosure that antibodies against any of the proteins of the present invention can be utilized to block the binding of ligands to the proteins and to target drugs or other agents (such as labels) to the cells expressing these proteins.

The present invention provides a novel cDNA sequence, a gene product (Pem) protein, and uses for this novel cDNA sequence and its associated Pem gene protein products. The cDNA sequence is 838 bp in length and contains a single long open reading frame that extends from bp 91 to 720 and predicts a protein containing 210 amino acids (FIG. 1). The numbers on the right of FIG. 1 refer to the nucleotide sequence, the numbers on the left indicate the predicted amino acid position. The first methionine present in the sequence is underlined. The polyadenylation signal consensus sequence, AATAAA, is also underlined. The (X) at the 3' end of the DNA sequence refers to a string of 14 adenylate residues of the poly(A) tail. Potential phosphorylation sites for cAMP/cGMP-dependent kinase (AG), protein kinase C (C), and casein kinase II (CK) were identified using intelliGenetics programs which identify the appropriate consensus senquences surrounding Ser or Thr for each of the kinases. The consensus polyadenylation sequence, AATAAA, is located 50 bp 5' of the poly(A) tract. The first methionine codon (91 bp from the 5' end) is surrounded by the Kozak consensus sequence ($G/_AXXATGG$) that provides an efficient translation start site (Kozak, 1986). Pem sense transcripts prepared using T7 polymerase and translated in a reticulocyte lysate, produce protein molecules of the predicted molecular weight (23 Kda, data not shown). Thus, the first methionine acts as a translation initiation site in in vitro transcription-translation experiments. The length of the Pem cDNA clone (839 bp, excluding the poly(A) tail) is similar to the size of Pem transcripts (0.9 kb) which have had their poly(A) tail removed (data not shown). Thus it is likely that the Pem cDNA clone is nearly full length.

The Pem protein is hydrophilic and contains no leader sequence, no N-linked glycosylation sites, nor any potential transmembrane spanning regions. Thus, Pem is not likely to be secreted or inserted into the cell membrane, but has properties of an intracellular protein. The predicted Pem protein contains consensus sequences for phosphorylation of Ser and Thr by protein kinase C, casein kinase and cAMP/cGMP-dependent kinase as noted in FIG. 1. Since DNA and predicted amino acid sequence searches of GenBank and Swiss Protein databases revealed no significant similarity to other known genes or gene products, Pem represents a new gene.

Having now generally described the invention a more complete understanding can be obtained by reference to the following specific examples. These examples are provided for purposes of illustration only and are not intended to be limiting unless otherwise specified.

EXAMPLE 1

Isolation, Characterization and Culture of Cells

A. Lymphoma Cell Lines. The isolation, characterization and culture requirements of the T lymphoma cell lines SL12.1, SL12.3, SL12.4 and somatic cell hybrids formed among them have been described in detail in Hays, et al., (1986) *Int. J. Cancer* 38:597–601; MacLeod, et al., (1984) *Cancer Research* 44:1784–1790; MacLeod, et al., (1985) *J. Nat. Cancer Inst* 74:875–882; MacLeod, et al., (1986) *Proc. Natl. Acad. Sci. USA* 83:6989–6993 and Weinroth, et al., (1985) *Cancer Research* 45:4804–4809; all of which are incorporated herein by reference.

The phenotypes of the SL12.3 and SL12.4 cell clones are summarized in Table 1. Transcript expression, surface protein expression, tumorigenicity and tumor type were determined by Northern analysis, flow cytometry and in vivo injection of cloned cells into syngeneic animals, respectively. TCR-$\beta$ 1.0 and 1.3 kb transcripts encode (D)-J-C and V-D-J-C sequences, respectively. The glucocorticoid response was determined by growth of the cells in 1 mM dexamethasone.

TABLE 1

| Phenotypic Characteristics of SL12.4 and SL12.3 Cell clones | | SL12.4 | SL12.3 |
|---|---|---|---|
| mRNA | Thy-1 | ++ | +++ |
|  | TCR-alpha | – | + |
|  | TCR-$\beta$ 1.0 kb | + | – |
|  | 1.3 kb | – | – |
|  | TCR-gamma | – | – |
|  | TCR-delta | – | – |
|  | CD3-gamma | + | – |
|  | CD3-delta | + | – |
|  | CD3-epsilon | + | +/– |
|  | CD3-zeta | + | + |
|  | CD2 | + | + |
|  | CD4 | – | – |
|  | CD8 | – | – |
| Surface Expression | Thy-1 | ++ | ++ |
|  | Pgp-1 | – | + |
|  | ThB | + | – |
|  | TL | + | + |
|  | T200 | + | + |
|  | H-2K$^k$ | – | – |
|  | IL2r | + | + |
|  | J11d | + | + |
|  | CD3-epsilon | – | – |
|  | Mel-14 | + | NT |
| Glucocorticoid Sensitivity |  | S | R |
| Tumorigenicity |  | Low | High |
| Tumor Type |  | Extra-Nodal (ovarian, muscle) | Diffuse |

R = cells resistant to lysis, S = sensitive to lysis.

SAKS cells (Gasson and Bourgeois, *J. Cell. Biol.* 96, 409–415 (1983) were obtained from Dr. Gasson. The lymphoma cells were cultured in Dulbecco's Modified Eagle's Medium supplemented with 10% fetal calf serum, glutamine, penicillin and streptomycin. Two human ovarian carcinoma cell lines 2008 (Disaea, et al., *Am. J. Obstet. Gynecol.* 114:979–989 (1972)) and COLO 316 (Woods, et al., *Cancer Res.* 39:4449–4459 (1979) were cultured in RPMI medium 1640 supplemented with 5% bovine calf serum, glutamine and 1% Fungibact (Irvine Scientific, Santa Ana, Calif.). When the cells were used to prepare RNA, they were harvested during exponential growth at a density near 5–8×10$^5$ cells per ml (Wilkinson, and MacLeod, *EMBO J.* 7:101–109, (1988). Splenocytes derived from BALB/c mice were seeded at 3×10$^6$ cells/ml and stimulated with 10 ug/ml ConA for two days before harvesting the RNA.

B. Co-cultivation of SL 12.4 cells and the thymic epithelial monolayers.

The co-cultivation conditions for SL 12.4 cells and the thymic epithelial monolayers. Briefly, SL 12.4 cells were seeded at a density such that their final concentration after the three day co-cultivation period was 1×10$^6$ cells/mi. TEL or TEPI were at confluency by the third day. The cells were grown in Dubellco's Modified Eagle's Medium containing 10% fetal calf serum and supplemented with glutamine and penicillin/streptomycin at 37° C.

C. Cell lines for 20.2 Expression Studies.

Cell lines from the following sources were used in the 20.2 expression studies: Embryonal carcinomas F9 and PCC4 (Bernstine, et al., (1973) *Proc. Natl. Acad. Sci. USA.* 70: 3899–3903, pituitary tumor ATt20 (Buonassisi, et al., (1962) *Proc. Natl. Acad. Sci. USA.* 48: 1184–1192), thymic epithelial TEPI (Beardsley, et al., (1983) *Proc. Natl. Acad. Sci. USA.* 80: 6005–6009), mammary epithelial MME (Evans, (1988) *Science* 240: 889–894)12.9), 3T3 (ATCC #92) and MEF were prepared according to Freshhey (Freshhey, (1983) *In Culture of Animal Cells.* Alan R. Liss, Inc. pp 99–110), B cell hybridoma PS.G8, B/T lymphoma WEHI-21, macrophage P388D1, thymic epithelial TEL, basophil RBL-1, T cell hybridoma 2H10$^y$, neuroblastoma N4TG1 myeloma S194/5, T lymphomas: SL12.3, RS 4.2, SAK8, BW5147, AKR1, EL-4, somatic cell hybrid SL12.3×SL12.4, and T cell hybridoma BO-4H.H9.1. The cells were cultured in Dulbecco's Modified Eagle's Medium supplemented with 10% fetal calf serum, glutamine, penicillin and streptomycin. Cells that were used to prepare RNA were harvested during exponential growth from cultures containing $5-8 \times 10^5$ cells per ml. Splenocytes obtained from BALB/c mice were seeded at $3 \times 10^6$ cells/ml in RPMI 1640 supplemented as above and stimulated with 10 ug/ml ConA for 6, 24, 48 or 72 hours before harvesting the RNA.

EXAMPLE 2

Cloning and Screening Strategy

Poly(A)+ mRNA from SL12.4 cells was used as a template to prepare double-stranded (ds) cDNA (Gubler and Hoffman, (1983) *Gene* 25:263–269). EcoRI linkers were added to the ds DNA which was previously methylated. Dephosphorlyated lambda gt10 arms (Stratagene) were ligated to the cDNA and packaged into lambda phage using Stratagene packaging extract according to the manufacturer's instructions (Huynh, et al., in D. Glover (ed.), (1984) *DNA Cloning Techniques: A Practical Approach.* IRL Press, Oxford, U.K.).

Subtraction hybridization was performed essentially as originally described by Hedrick, et al., (1984) *Nature* 308:149–153 and Timberlake, (1980) *Dev. Biol.* 78:497–503. Single stranded cDNA was prepared from 10 mg poly(A)+ SL124 RNA using 250 mC of $^{32}$P dCTP (Amersham) in the presence of 100 ug/ml of actinomycin D and hybridized to a Rot of 1260 (mol of nucleotide per liter×sec) with 25 mg poly(A)+ RNA from SL12.3 cells in a volume of 8 ml at 68° C. for 18 hours. After hybridization, the ss cDNA was collected by chromatography through a hydroxyapatite column. From 1 ug of starting SL12.4 cDNA, approximately 120 ng (12% of the input cDNA containing $3 \times 10^7$ cpm) was recovered and used to probe two 150 mm nitrocellulose filters containing 20,000 lambda gt10 plaques per filter. The first of two duplicate filter lifts from the SL12.4 lambda gt10 library was probed with total cDNA from SL12.3 mRNA, and the second filter lift was probed with the SL12.4 subtraction enriched cDNA prepared as described above. The strategy used was similar to that used by Filmus et al. The plaque purified lambda phage clones were identified as SL12.4-specific by two screenings (using separately prepared subtracted probes), subsequently Northern analysis was used to confirm that the clone hybridized only to mRNA from SL12.4 cells and not SL12.3 cells. The cDNA inserts were removed from lambda DNA by digestion with the restriction enzymes Hind III and Bgl II, isolated in low melting point agarose (Sea Kem) and subcloned into the plasmid vector pT7/T3 (Bethesda Research Laboratory) digested with Hind III and BamHI. The inserts could not be excised from the phage with EcoRI because the EcoRI sites were damaged in all of the isolates Kuziel, et al., (1987) *Nucl. Acid Res.* 15:3181.

Using the Pem cDNA, 15 additional clones were obtained from a lambda ZAPII SL12 cDNA library. These clones cover the full length of the mature mRNA transcript.

EXAMPLE 3

Northern Blot Analysis

Total cellular RNA was isolated from cell lines and tissues by the guanidine isothiocyanate method (Maniatis, et al., (1983) In *Molecular Cloning: A Laboratory Manual.* Cold Spring Harbor Laboratory Press, Cold Spring Harbor, N.Y., modified as described (Wilkinson, et al., (1988) *EMBO J.* 7:101–109). Equal loading and transfer of RNA per lane was assessed by acridine orange staining (Maniatis, et al., (1983) In *Molecular Cloning: A Laboratory Manual.* Cold Spring Harbor Laboratory Press, Cold Spring Harbor, N.Y.) and by hybridization with actin, CHO-A and/or cyclophillin cDNA. For tissues, the method was modified such that the RNA pellet obtained after centrifugation in cesium chloride was resuspended in 10mM Tris (pH 8), 0.5% SDS, 5 mM EDTA, followed by two extractions with phenol:chloroform:iso-amyl alcohol (24:24:1) and two extractions with chloroform:2-butanol:iso-amyl alcohol (20:5:1). For RNA blots, 10 mg of RNA was electrophoresed in 1% agarose-formaldehyde gels and transferred to Nytran membranes (Maniatis et al., 1982). The Northern blots were hybridized with random oligomer primed $^{32}$p-labeled cDNA inserts in the presence of 10% dextran sulphate and 50% formamide for 12–18 hr at 42° C. (Meinkoth and Wahl, 1984) To remove the labeled probe, RNA blots were washed with 0.1X SSPE and 0.1% SDS at 90° C. (Maniatis, et al. (1982) in "Molecular Cloning: A Laboratory Manual", Cold Spring Harbor Laboratory Press, Cold Spring Harbor, N.Y.), allowed to cool to room temperature, air-dried, and stored under vacuum until hybridized again. RNA sizes were determined by comparison with BRL RNA high and low molecular weight ladders.

EXAMPLE 4

Southern Blot Analysis

Total cellular DNA was isolated from cells, T lymphoma and murine-hamster somatic cell hybrids and tissues from other species was digested with the restriction enzyme Eco R.I. Twenty micro g of digested DNA was applied to each lane of a 0.7% agarose gel and electrophoresed and blotted onto Nytran supports essentially as described (Meinkoth and Wahl, (1984) *Anal. Biochem.* 13:267–284), hybridized and washed as described for Northern blot analysis.

B. Southern blot analysis of 20.2

Southern blot analysis of 20.2 was performed as above except as noted below.

Total cellular DNA was isolated from SL12.4 cells, murine and hamster liver and from somatic cell hybrids. DNA from chicken and human liver was obtained commercially from Clonetec, Palo Alto, Calif. The DNA was digested with the restriction enzymes noted in the Examples according to the supplier's conditions. Ten ug of digested DNA was applied to each lane of a 0.8% agarose gel and electrophoresed in Tris acetate buffer for at least 48 hr and blotted onto Nytran supports, hybridized and washed as described for Northern blot analysis. The blots containing DNA from other species was washed at a lower stringency, the final wash was carried out at romm temperature with 2X SSPE.

Total cellular DNA was isolated as described (Maniatis et al., 1982), digested with the restriction enzymes Eco R.I. Twenty micrograms of digested DNA was applied to each lane of a 0.7% agarose gel and electrophoresed in Tris acetate buffer, blotted onto a Nytran membrane essentially as described (Maniatis et al., 1982), and washed as described for Northern blots.

EXAMPLE 5

DNA Sequence Analysis

A restriction endonuclease map was determined from the Pem cDNA clone and fragments subcloned into pT7T3; the plasmid was purified over a cesium chloride gradient and directly sequenced by double-stranded dideoxy sequencing methods using Sequenase reagents (U.S. Biochemical Corp., Cleveland, Ohio). Part of the sequence was determined using primers to the host plasmid and other specific oligonucleotide primers (17mers) were prepared to the cDNA in the UCSD Cancer Center Core Molecular Biology Facility. Both DNA strands were sequenced in their entirety and all sequences were determined in at least two reactions performed in duplicate. Microgenie and IntelliGenetics computer programs were used to assemble the overlapping sequence information and perform the initial analysis of the DNA sequence. The properties of the predicted protein were assessed using the Prosite program from IntelliGenetics. The DNA and predicted protein sequence was used to search for similarities in the Swiss Protein and EMBL databases.

EXAMPLE 6 cDNA and Predicted Protein Sequence of Pem

In order to determine the cDNA and the protein sequence of the protein encoded by the Pem gene, novel cDNAs corresponding to genes involved in differentiation and/or neoplasia were sought. Toward that end, two closely related T-lymphoma cell clones SL12.4 and SL12.3 (MacLeod et al., (1984) Cancer Res. 44: 1784–1790) which differ in maturation level and tumorigenic properties were selected. On the basis of an analysis 10 cell surface antigens and 12 specific mRNAs, the cell clones represent distinct stages or lineages of T cell development (MacLeod et al., (1984) Cancer Res. 44: 1784–1790; MacLeod, et al. (1985) J. Natl. Cancer Inst. 74: 875–882; MacLeod, et al. (1986) Proc. Natl. Acad. Sci. USA 83: 6989–6993; Hays et al., (1986) Int. J. Cancer 38: 597–601; McLeod et al., (1990) Cell Growth Differ. 1: 271–279). One cDNA clone, 20.2, identifies transcripts expressed in placenta and embryos and has been termed Pem.

The cDNA sequence is 838 bp in length and contains a single long open reading frame that extends from bp 91 to 720 and predicts a protein containing 210 amino acids (FIG. 1). The numbers on the right of the figure refer to the nucleotide sequence, the numbers on the left indicate the predicted amino acid position. The first methionine present in the sequence is underlined. The polyadenylation signal consensus sequence, AATAAA, is also underlined. The (X) at the 3' end of the DNA sequence refers to a string of 14 adenylate residues of the poly(A) tail. Potential phosphorylation sites for cAMP/cGMP-dependent kinase (AG), protein kinase C (C), and casein kinase II (CK) were identified using intelliGenetics programs which identify the appropriate consensus sequences surrounding Ser or Thr for each of the kinases. The consensus polyadenylation sequence, AATAAA, is located 50 bp 5' of the poly(A) tract. The first methionine codon (91 bp from the 5' end) is surrounded by the Kozak consensus sequence ($G/_AXX$-ATGG) that provides an efficient translation start site (Kozak (1986) Cell 44: 283–292). Pem sense transcripts prepared using T7 polymerase and translated in a reticulocyte lysate, produce protein molecules of the predicted molecular weight (23 Kda, data not shown). Thus, the first methionine acts as a translation initiation site in in vitro transcription-translation experiments. The length of the Pem cDNA clone (838 bp, excluding the poly(A) tail) is similar to the size of Pem transcripts (0.9 kb) which have had their poly(A) tail removed (data not shown). Thus it is likely that the Pem cDNA clone is nearly full length.

The Pem protein is hydrophilic and contains no leader sequence, no N-linked glycosylation sites, nor any potential transmembrane spanning regions. Thus, Pem is not likely to be secreted or inserted into the cell membrane, but has properties of an intracellular protein. The predicted Pem protein contains consensus sequences for phosphorylation of Ser and Thr by protein kinase C, casein kinase and cAMP/cGMP-dependent kinase as noted in FIG. 1. Since DNA and predicted amino acid sequence searches of GenBank and Swiss Protein databases revealed no significant similarity to other known genes or gene products, Pem represents a new gene.

EXAMPLE 7

Expression of Pem Transcripts

In order to ascertain the expression of Pem transcripts in immortalized and transformed cell lines, northern analysis was used to identify the tissues and cell types which express Pem transcripts. Pem transcripts are abundant in a T lymphoma cell line, but they are not detectable in lymphoid tissue from adult thymus, quiescent or activated splenocytes, gut associated lymphoid tissue or bone marrow, and are not detectable in adult brain, liver, large intestine, or ovary. Further, Pem transcripts were not found in pancreas, heart, lung, stomach, kidney or pituitary.

Since the Pem cDNA clone was isolated from a transformed cell line (SL12.4), Pem gene expression was assessed in other immortalized and transformed lines (FIG. 2). To obtain the Pem mRNA expression in all lines, northern blots were probed with $^{32}P$ labeled Pem inserts to assess the expression of Pem mRNA in the following murine cell lines: F9, PCC4 (embryonal carcinomas); ATt20 (pituitary); TEPI (thymic epithelial); MME (mammary epithelial); 3T3 (immortalized fibroblast); MEF (normal murine embryo fibroblasts); SL12.4 (T-lymphoma); PS.G8 (B cell hybridoma); WEHI-21 (B/T-lymphoma); P388D1 (macrophage); TEL (thymic epithelial); RBL-1 (basophil); 2H10$^v$ (T cell hybridoma); N4TG1 (neuroblastoma); S194/5 (myeloma); SL12.3, RS4.2, SAKS, BW5147, AKR1, EL-4

(T-lymphomas); SL12.3×SL12.4 (somatic cell hybrid); and BO-4H.H.9.1 (T cell hybridoma). Similar loading and transfer of RNA in all lanes was assessed by acridine orange staining of 18S and 28S rRNA, and by hybridization of the blot with a $^{32}$p labeled cyclophillin (Cy) probe (Takahashi et al., (1989) *Nature* 337: 473–475) which recognizes transcripts present at similar levels in most murine cell lines.

Two embryonal carcinoma cell lines (F9 and PCC4), which have characteristics of pluripotent stem cells, express the Pem gene, but in strikingly different amounts. Immortalized 3T3 fibroblasts express Pem abundantly, whilst normal embryo fibroblast express at least 30-fold less Pem mRNA. Pem is expressed in cell lines of neuronal, pituitary, macrophage and mammary epithelial origin. In contrast, Pem transcripts are virtually undetectable in thymic epithelial cell lines and in most B and T cell tumor and hybridoma cell lines tested, although one B cell hybridoma (PS.GS) and two T lymphoma cell lines (EL4 and SL12.4) express Pem transcripts (FIG. 2). FIG. 2 shows that the 1.1-kb transcript is the most prominent transcript; however, some cells express an additional 3-kb mRNA. Both the 1.1 and 3-kb transcripts are enriched in poly(A)-selected RNA and are present in the cytoplasmic compartment in SL12.4 cells.

The lack of any obvious pattern of lineage specificity for Pem gene expression and the large variability in the amount of mRNA in the cell lines raises the possibility that the genes have been randomly lost, inactivated, translocated, or amplified either in vivo or after prolonged in vitro culture. Southern analysis has previously shown that Pem genes showed no detectable differences in band intensity or size between SL12.3 (Pem−) and SL12.4 (Pem+) cells, nor in another (Pem−) T lymphoma cell line, SAK8 (MacLeod et al., (1990) *Cell Growth Differ.* 1: 271–279). DNA has been subsequently tested from several of the cell lines expressing large amounts of Pem mRNA (SL12.4, ATt20, F9, MME, N4TG1, and EL4) and no differences in band intensity (copy number) or size were detected. Thus, it is unlikely that gene deletions, major genetic rearrangements, or gene amplification events are responsible for the differences in PEM mRNA accumulation in the cell lines.

EXAMPLE 8

Pem Gene Expression in Embryonic Development

Figure 3:
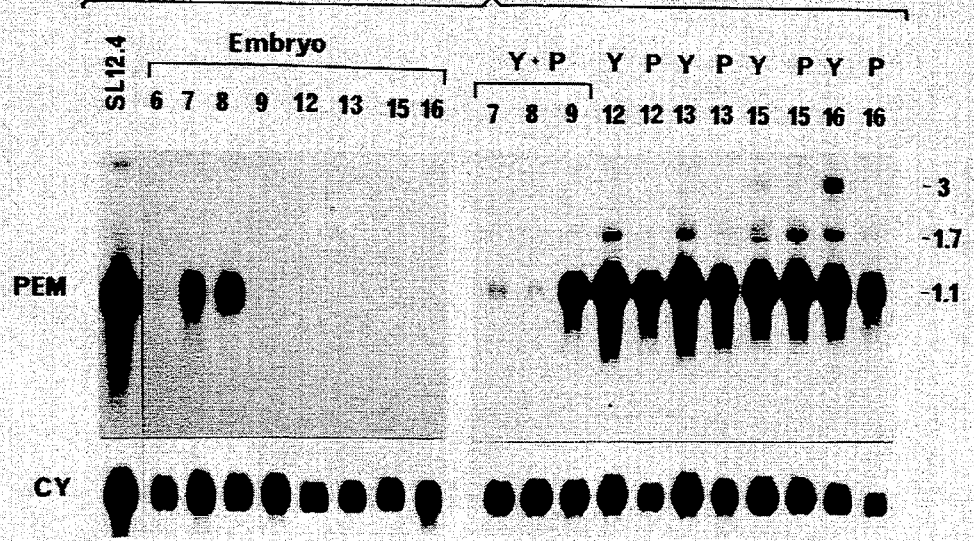
FIG. 3 demonstrates Pem mRNA expression during fetal development.

The pattern of Pem gene expression is similar to oncofetal genes since Pem transcripts are present in transformed and immortalized cell lines, in embryonal carcinoma stem cells, but not in adult tissues (Ruddon (1987) Gene Derepression in Cancer Cells, In Cancer Biology, Oxford University Press, New York, pp 431–436). To further explore the possibility that Pem belongs to this class of genes, transcript levels were assessed in both embryos and in extraembryonic tissues at several stages of murine development. RNA was prepared from embryo, placenta (P), and yolk sac (Y) at the times of gestation indicated on FIG. 3. FIG. 3 shows that Pem transcripts are detectable as early as 6 days in embryonic development. Day 6 embryos include extra-embryonic tissue. Pem mRNA becomes abundant on day 7 or 8, but expression is sharply curtailed by day 9 and thereafter, although a faint signal is typically observed (FIG. 3). In contrast, Pem transcripts are barely detectable in day 7 or 8 placenta and yolk sac, but increase to abundant levels on day 9, and all subsequent stages. Day 10 and 18 embryo, placenta, and yolk sac (not shown) possessed a similar pattern of Pem mRNA expression as days 12–16. The blots were probed as described in FIG. 2. The Pem gene expression patterns in embryonic and extraembryonic tissue lead to two significant conclusions: 1) Pem mRNA accumulates at high levels only briefly in embryos in toto (7 and 8 days) although it may persist in specific embryonic lineages at later stages; 2) The expression of Pem mRNA in embryos is reciprocal to that observed in extraembryonic tissue.

EXAMPLE 9

Pem is an Oncofetal Gene

The Pem gene is expressed in a stage-specific manner during embryogenesis and it is expressed in a wide variety of immortalized and transformed cell lines. It is not detectably expressed in any adult tissues tested. Since these unusual expression characteristics are those expected of oncofetal genes (Ruddon (1987) Gene Derepression in Cancer Cells, in *Cancer Biology*, Oxford University Press, New York, pp 431–436), Pem may be a useful marker of immortalized cells and/or cells participating in early murine development. The observation that Pem transcripts decrease precipitously in day 9 embryos, the same point of gestation at which they become abundant in placenta and yolk sac, suggests the possibility that Pem+ cells migrate from the embryonic to the extraembryonic compartment. Cells from the extraembryonic mesoderm (derived from the inner cell mass) give rise to placental and yolk sac cells, and thus have the characteristics expected of such a migrating cell. Although the Pem gene is specifically expressed during fetal development, it cannot be ruled out that it may also function in the adult. The Pem gene may be expressed by numerically infrequent or transient progenitor cells present in adult tissue. Since both adult and fetal progenitor cells are thought to be the targets of the transformation/immortalization process, (Pierce and Speers, (1988) *Cancer Res.* 48: 1996–2004), the observation that Pem mRNA is expressed by numerous immortalized and transformed cell lines is consistant with this concept. Deregulation resulting in overexpression or constitutive expression of Pem in immortalized cells might thereby contribute to their capacity for continuous cell proliferation.

In order to prevent or control the abnormal proliferation induced by the overexpressionor constitutive expression of Pem, homologous recombinant gene therapy or targeted gene inactivation may be utilized to inhibit the function of the gene or the expression of a functional gene product. To this end, genomic clones of the Pem gene are utilized. The Pem gene is inactivated by inserting a selective marker within the gene in a position which inactivates the capacity of the gene to encode a functional marker or the capacity for the expression of a functional marker. The mutated gene is then transferred by electroporation or microinjection into an embryonic stem cell or an established cell line of same. Cells in which the selective marker is appropriately incorporated are selected, and transferred into the blastocyst of an individual. Individuals may be selected which comprise either one or both alleles of the Pem gene so transformed.

One skilled in the art will readily appreciate that the present invention is well adapted to carry out the objects and obtain the ends and advantages mentioned, as well as those inherent therein. The components, methods, procedures and techniques described herein are presently representative of the preferred embodiments, are intended to be exemplary, and are not intended as limitations on the scope of the present invention. Changes therein and other uses will occur to those skilled in the art which are encompassed within the spirit of the invention and are defined by the scope of the appended claims.

What is claimed as new and is desired to be covered under Letters Patent is:

1. A cDNA probe comprising the nucleotide sequence shown in Seq. id No. 1.

2. An expression vehicle which comprises a DNA sequence coding for the Pem (Seq. id. No. 1) protein, wherein said expression vehicle is capable of replication in a host which comprises, in operable linkage;
   a) an origin of replication;
   b) a promoter; and
   c) a DNA sequence coding for Pem (Seq. id. No. 1) protein.

3. The expression vehicle of claim 2, wherein said expression vehicle is a plasmid capable of replication in a host which comprises, in operable linkage:
   a) an origin of replication;
   b) a promoter; and
   c) a DNA sequence coding for Pem (Seq. id. No. 1) protein.

4. The expression vehicle of claim 3, wherein said expression vehicle is a plasmid capable of replication in a prokaryotic host which comprises, in operable linkage:
   a) a prokaryotic origin of replication;
   b) a prokaryotic promoter; and
   c) a DNA sequence coding for Pem (Seq. id. No. 1) protein.

5. A vector comprising a DNA sequence coding for Pem (Seq. id. No. 1) protein, wherein said vector is capable of replication in a host which comprises, in operable linkage;
   a) an origin of replication;
   b) a promoter; and
   c) a DNA sequence coding for Pem (Seq. id. No. 1) protein.

6. The vector of claim 5 wherein said vector is isolated from the group consisting of a plasmid, a phage and a cosmid.

7. The vector of claim 6, wherein said vector is pT7T3-20.2 having ATCC Accession number 68304.

8. A host transformed with a recombinant DNA molecule wherein said recombinant DNA molecule comprises a DNA sequence coding for the Pem (Seq. id. No. 1) protein.

9. The host of claim 8 which is *E. coli*.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 838 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( B ) STRAIN: AKR1 Jackson
        ( C ) INDIVIDUAL ISOLATE: SL12 cell line
        ( D ) DEVELOPMENTAL STAGE: Bone marrow- adult
        ( F ) TISSUE TYPE: Lymphoma
        ( G ) CELL TYPE: T-cell
        ( H ) CELL LINE: SL12.4 clone ( i x ) FEATURE:
        ( D ) OTHER INFORMATION:
            N at nucleotide 838 represents a polyA string ( x i ) SEQUENCE DESCRIPTION: SEQ ID NO:1:

```
GAAGAGCCAA  ACAGCCATCT  CCCTGCACAG  TCCTTCAAGC  TCACCTCCTG  CCTTCCGTGG        60

ACAAGAGGAA  GCACAAAGAA  TCATCCAGGT  ATGGAAGCTG  AGGGTTCCAG  CCGCAAGGTC       120

ACCAGGCTAC  TCCGCCTGGG  AGTCAAGGAA  GACTCGGAAG  AACAGCATGA  TGTGAAAGCA       180

GAGGCTTTCT  TCCAGGCTGG  AGAGGGGAGA  GATGAGCAAG  GTGCACAGGG  CCAGCCTGGA       240

GTGGGAGCGG  TGGGAACAGA  AGGCGAAGGA  GAAGAATTAA  ATGGAGGAAA  AGGCCACTTT       300

GGTCCTGGTG  CTCCTGGTCC  TATGGGTGAT  GGGGACAAGG  ATAGTGGCAC  CAGGGCTGGT       360

GGTGTGGAGC  AGGAACAAAA  TGAGCCAGTT  GCTGAGGGCA  CTGAGAGCCA  GGAGAATGGA       420

AATCCTGGGG  GTAGGCAGAT  GCCCCTCCAG  GGCTCTAGGT  TCGCCCAGCA  TCGACTGAGG       480

GAACTGGAGT  CCATTTTGCA  GCGCACTAAT  TCCTTTGATG  TCCCAAGGGA  GGATCTTGAT       540
```

```
AGACTGATGG ATGCCTGTGT GTCCAGAGTG CAGAATTGGT TTAAGATCAG GAGGGCTGCG    600
GCCAGAAGAA ACAGGAGGAG GGCAACACCA GTCCCTGAAC ATTTTAGAGG AACATTCGAG    660
TGTCCTGCTT GTCGTGGAGT GAGATGGGGA GAAAGATGCC CTTTTGCGAC ACCGAGATTT    720
TGATTTGATC ACATATGCCG GCTATGACAG CCCTTACTTT TCAAGAATTC AGCAATAAAG    780
AGGTGGATTC CCAGTATGTT TGTTCCATTA CCTCTATGAT TATTAAAATA TTGATACN     838
                                                    * * * * *
```

UNITED STATES PATENT AND TRADEMARK OFFICE
CERTIFICATE OF CORRECTION

PATENT NO.   : 5,342,761
DATED        : August 30, 1994
INVENTOR(S)  : Carol L. MacLeod Page 1 of 3

It is certified that error appears in the above-identified patent and that said Letters Patent is hereby corrected as shown below:

Figure 1A,
Line ending 462, please replace "CTC CAG GGC TCT AGG TTC" with
-- TCC AGG GCT CTA GGT TCG --.

Figure 1B,
Line ending 504, please replace "GCC CAG CAT" with -- CCC AGC TAT --.
Line ending 630, please replace "AAC" with -- ACC --.

Column 1,
Line 48, "161-111" should read -- 767-772 --.
Line 63, "a-fetoprotein" should read -- α-fetoprotein --.

Column 3,
Line 11, "hematopoeitic" should read -- hematopoietic --.

Column 5,
Line 16, "*subtillis*" should read -- *subtilis* --.

Column 6,
Line 14, "$^{32}$p" should read -- $^{32}$u.c. --.
Line 47, "prominant" should read -- prominent --.
Line 64, "KDA" should read -- RNA --.

Column 7,
Line 7, "838" should read -- 839 --.

Column 8,
Line 42, "SAKS" should read -- SAK8 --.
Line 43, please insert a comma after the words "(1983)".
Line 49, please insert a comma after the word "(1979)".
Line 56, please insert a comma after the word "(1988)".
Line 67, "Dubellco's" should read -- Dulbecco's --.

UNITED STATES PATENT AND TRADEMARK OFFICE
CERTIFICATE OF CORRECTION

PATENT NO.    : 5,342,761
DATED         : August 30, 1994
INVENTOR(S)   : Carol L. MacLeod It is certified that error appears in the above-identified patent and that said Letters Patent is hereby corrected as shown below:

Column 9,
Line 13, "Freshhey" should read -- Freshney -- in both places.
Line 17, please insert a comma after the words "N4TG1".
Line 37, "Dephosphorlyated" should read -- Dephosphorylated --.

Column 10,
Line 39, "$^{32}$p-labeled" should read -- $^{32}$u.c.-labeled --.
Line 41, please insert a period after the words "1984)".

Column 11,
Line 10, "romm" should read -- room --.
Line 52, please insert the word -- of -- between the words "sis" and "10".

Column 12,
Line 68, "SAKS" should read -- SAK8 --.

Column 13,
Line 19, "(PS.GS)" should read -- (PS.G8) --.
Line 53, "Cancer Biology" should read -- Cancer Biology --.

Column 14,
Line 42, "consistant" should read -- consistent --.
Line 48, Overexpressionor" should read -- overexpression or --.

Column 15,
Line 12, please insert a period after the word "id".
Line 16, please delete the semi-colon after the word "linkage" and replace it with a colon.

Column 16,
Line 12, please delete the semi-colon after the word "linkage" and replace it with a colon.
Line 26, please insert a comma after the number "8".

UNITED STATES PATENT AND TRADEMARK OFFICE
CERTIFICATE OF CORRECTION

PATENT NO. : 5,342,761
DATED : August 30, 1994
INVENTOR(S) : Carol L. MacLeod

It is certified that error appears in the above-identified patent and that said Letters Patent is hereby corrected as shown below:

In the Sequence Listing, line ending 480, please replace "GCCCCTCCAG GGCTCTAGGT TCGCCCAGCA TCGACTGAGG" with -- GCCCTCCAGG GCTCTAGGTT CGCCCAGCTA TCGACTGAGG --.

In the Sequence Listing, line ending 660, please replace "ACAGGAGGAG" with -- CCAGGAGGAG --.

Signed and Sealed this

Twenty-fifth Day of September, 2001

Attest:

NICHOLAS P. GODICI
Attesting Officer    Acting Director of the United States Patent and Trademark Office